United States Patent
Zhang et al.

(10) Patent No.: US 12,390,443 B2
(45) Date of Patent: Aug. 19, 2025

(54) APPLICATIONS OF BUTYROLACTONE-I IN PREPARING MEDICINE FOR PREVENTING NEUROINFLAMMATION AND/OR MEMORY AND COGNITIVE DISORDERS

(71) Applicants: GUANGDONG OCEAN UNIVERSITY, Zhanjiang (CN); SHENZHEN INSTITUTE OF GUANGDONG OCEAN UNIVERSITY, Shenzhen (CN)

(72) Inventors: Yi Zhang, Zhanjiang (CN); Yingying Nie, Shenzhen (CN); Yayue Liu, Zhanjiang (CN); Xiaoxiang Ma, Dongguan (CN); Jinyue Liang, Yunfu (CN); Yanmei Li, Zhaoqing (CN); Yuan Wang, Dongguan (CN); Zhiyou Yang, Zhanjiang (CN); Yongping Zhang, Zhanjiang (CN); Cai Song, Shenzhen (CN); Pengzhi Hong, Zhanjiang (CN); Zhongji Qian, Zhanjiang (CN)

(73) Assignees: GUANDONG OCEAN UNIVERSITY, Zhanjiang (CN); SHENZHEN INSTITUTE OF GUANGDONG OCEAN UNIVERSITY, Shenzhen (CN)

(*) Notice: Subject to any disclaimer, the term of this patent is extended or adjusted under 35 U.S.C. 154(b) by 855 days.

(21) Appl. No.: 17/675,405

(22) Filed: Feb. 18, 2022

(65) Prior Publication Data
US 2022/0249435 A1 Aug. 11, 2022

Related U.S. Application Data

(63) Continuation of application No. PCT/CN2021/077625, filed on Feb. 24, 2021.

(30) Foreign Application Priority Data

Feb. 9, 2021 (CN) .......................... 202110176567.4

(51) Int. Cl.
*A61K 31/365* (2006.01)
*A61P 25/28* (2006.01)

(52) U.S. Cl.
CPC ............ *A61K 31/365* (2013.01); *A61P 25/28* (2018.01)

(58) Field of Classification Search
CPC .............................. A61K 31/365; A61P 25/28
See application file for complete search history.

(56) References Cited

FOREIGN PATENT DOCUMENTS

CN 110777176 A 2/2020

OTHER PUBLICATIONS

Cai et. al., "Polysaccharides from Ganoderma lucidum attenuate microglia-mediated neuroinflammation and modulate microglial phagocytosis and behavioural response", Journal of Neuroinflammation (Year: 2017).*
Mhalhel et. al., ("Zebrafish: A Model Deciphering the Impact of Flavonoids on Neurodegenerative Disorders", Cells, 12 (Year: 2023).*
Zhang et. al., "Butyrolactone-I from Coral-Derived Fungus Aspergillus terreus Attenuates Neuro-Inflammatory Response via Suppression of NF-κB Pathway in BV-2 Cells", Mar. Drugs., 16 (Year: 2018).*

* cited by examiner

*Primary Examiner* — Jeffrey H Murray
*Assistant Examiner* — Daniel John Burkett
(74) *Attorney, Agent, or Firm* — Cooper Legal Group, LLC

(57) ABSTRACT

Applications of butyrolactone-I in preparation of medicine for preventing aluminum-induced neuroinflammation and/or memory and cognitive disorder in zebrafish are provided. The applications have proven that at the animal level, butyrolactone-I may prevent aluminum-induced neuroinflammation and improve memory and cognitive disorder through the targets of antioxidation-inhibition of acetylcholinesterase activity-antiinflammation-regulation of intestinal flora disorder, and that butyrolactone-I may be used to prepare medicine for preventing aluminum-induced neuroinflammation and/or improving memory and cognitive disorder, thus providing a feasible scheme for preventing neurodegenerative diseases in clinical medicine.

5 Claims, 8 Drawing Sheets
Specification includes a Sequence Listing.

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Specific primer sequence-357F

<400> SEQUENCE: 1
actcctacgg raggcagcag                                              20

<210> SEQ ID NO 2
<211> LENGTH: 20
<212> TYPE: DNA
<213> ORGANISM: Artificial Sequence
<220> FEATURE:
<223> OTHER INFORMATION: Specific primer sequence-806R

<400> SEQUENCE: 2
ggactachvg ggtwtctaat                                              20

<210> SEQ ID NO 3
<211> LENGTH: 26
<212> TYPE: DNA
<213> ORGANISM: Artificial Sequence
<220> FEATURE:
<223> OTHER INFORMATION: Fragment of F inner primer

<400> SEQUENCE: 3
ttccctacac gacgctcttc cgatct                                       26
```

```
<210> SEQ ID NO 4
<211> LENGTH: 29
<212> TYPE: DNA
<213> ORGANISM: Artificial Sequence
<220> FEATURE:
<223> OTHER INFORMATION: Fragment of F outer primer

<400> SEQUENCE: 4
aatgatacgg cgaccaccga gatctacac                                29

<210> SEQ ID NO 5
<211> LENGTH: 18
<212> TYPE: DNA
<213> ORGANISM: Artificial Sequence
<220> FEATURE:
<223> OTHER INFORMATION: Another fragment of F outer primer

<400> SEQUENCE: 5
tcttcctaca cgacgctc                                            18

<210> SEQ ID NO 6
<211> LENGTH: 26
<212> TYPE: DNA
<213> ORGANISM: Artificial Sequence
<220> FEATURE:
<223> OTHER INFORMATION: Fragment of R inner primer

<400> SEQUENCE: 6
gagttccttg gcacccgaga attcca                                   26

<210> SEQ ID NO 7
<211> LENGTH: 24
<212> TYPE: DNA
<213> ORGANISM: Artificial Sequence
<220> FEATURE:
<223> OTHER INFORMATION: Fragment of R outer primer

<400> SEQUENCE: 7
caagcagaag acggcatacg agat                                     24

<210> SEQ ID NO 8
<211> LENGTH: 27
<212> TYPE: DNA
<213> ORGANISM: Artificial Sequence
<220> FEATURE:
<223> OTHER INFORMATION: Another fragment of R outer primer

<400> SEQUENCE: 8
gtgactggag ttccttggca cccgaga                                  27
```

APPLICATIONS OF BUTYROLACTONE-I IN PREPARING MEDICINE FOR PREVENTING NEUROINFLAMMATION AND/OR MEMORY AND COGNITIVE DISORDERS

TECHNICAL FIELD

The invention relates to the field of pharmaceutical technology, and more particularly to applications of butyrolactone-I in preparing medicine for preventing aluminum-induced neuroinflammation and/or memory and cognitive disorders of zebrafish.

BACKGROUND

Neurodegenerative disorders (NDs) refer to a kind of chronic and progressive nervous system disease caused by the loss of neurons in the brain and spinal cord, which leads to the disorder of memory, mobility and consciousness, such as Alzheimer's disease (AD) and Parkinson's disease (PD). As the aging population and environmental degradation are getting worse, the threat of neurodegenerative diseases to humans is becoming increasingly serious.

Modern neuroimmunology study shows that oxidative stress and inflammation play a critical and extensive role in the injury and apoptosis of neurons. It has been found in previous studies that many factors, such as chronic inflammation, Aβ (amyloid β-protein), pathogen infection in peripheral or brain regions, may over activate microglia in brain; pro-inflammatory factors and free radicals released by microglia may initiate and amplify the injury response of neurons, and reduce the neurotrophic factor produced by astrocytes. Oxidative stress and inflammatory reaction may activate each other cyclically, thus aggravating the damage of inflammation to neurons, which in turn activates microglia, forming a vicious circle, and finally causing the death or dysfunction of neurons and astrocytes. In addition to Aβ, the formation of neurofibrillary tangles, another important pathological marker of AD, is also importantly related to oxidative stress and inflammation activating kinase cdk5 (cyclin-dependent kinase) and leading to hyperphosphorylation of Tau protein (microtubule-associated protein tau). In addition, a growing number of studies also show that intestinal microbiota is closely related to NDs.

However, at present, clinical medicines for preventing and treating NDs have limited efficacies. For example, donepezil and compound levodopa may only partially relieve NDs symptoms, but may not reverse or stop its deterioration. The pathogenesis of NDs is complex, and the development of anti-NDs medicine for isolated targets (such as Aβ and Tau) has failed over and over again. Therefore, it has become an important new approach to develop new anti-NDs medicine by inhibiting inflammation and oxidative stress to protect neurons and intervene in the early stage of the disease.

SUMMARY

The objective of the invention is to provide the applications of butyrolactone-I in preparing medicine for preventing aluminum-induced neuroinflammation and/or memory and cognitive disorder of zebrafish, butyrolactone-I may improve aluminum-induced neuroinflammation and memory and cognitive disorder of zebrafish, and has a promising application prospect in preparing medicine for resisting neuroinflammation and memory and cognitive disorder.

In order to achieve the above objective, the invention provides the following schemes:

the invention provides the applications of butyrolactone-I in preparing medicine for preventing aluminum-induced neuroinflammation and/or memory and cognitive disorder of zebrafish.

Preferably, butyrolactone-I may prevent aluminum-induced neuroinflammation and/or memory and cognitive disorder of zebrafish by inhibiting acetylcholinesterase (AChE) activity.

Preferably, butyrolactone-I may prevent aluminum-induced neuroinflammation and/or memory and cognitive disorder of zebrafish by increasing the production of GSH (abbreviation for glutathione) in brain.

Preferably, butyrolactone-I may prevent aluminum-induced neuroinflammation and/or memory and cognitive disorder of zebrafish by reducing the levels of inflammatory factor IL-1β (abbreviation for jilted eukin-1β) in brain and peripheral tissues and/or reducing the levels of inflammatory factor TNF-α (abbreviation for tumor necrosis factor α) in brain tissues of zebrafish.

Preferably, butyrolactone-I may prevent aluminum-induced neuroinflammation and/or memory and cognitive disorder of zebrafish by regulating the disturbance of intestinal flora of zebrafish.

The invention discloses the following technical effects:

The butyrolactone-I disclosed by the invention is derived from marine fungus *Aspergillus terreus* C23-3, and butyrolactone-I is fermented by this fungus and then separated and purified. After animal experiments, the results show that butyrolactone-I may obviously improve the memory and cognitive disorder of zebrafish caused by aluminum trichloride at the behavioral level; butyrolactone-I may significantly relieve the nerve inflammation of zebrafish caused by aluminum trichloride and inhibit the activity of acetylcholinesterase in brain at the biochemical level; butyrolactone-I may regulate the intestinal flora disorder of zebrafish caused by aluminum trichloride at the molecular level. It is proved that butyrolactone-I may prevent aluminum-induced neuroinflammation and improve memory and cognitive disorder through the targets of antioxidation-inhibition of acetylcholinesterase activity-antiinflammation-regulation of intestinal flora disorder. The experiment of the invention proves that butyrolactone-I may be applied to the preparation of medicine for preventing neuroinflammation and memory and cognitive disorder caused by aluminum, thereby providing a feasible scheme for preventing neurodegenerative diseases in clinical medicine.

BRIEF DESCRIPTION OF DRAWINGS

FIG. 1A shows incubation period of zebrafish entering EC area for the first time; FIG. 1B shows average speed of zebrafish; and FIG. 1C shows the number of times zebrafish enter EC area;

FIG. 3A shows the level of GSH in brain tissue of zebrafish; FIG. 3B shows AChE activity in brain tissue of zebrafish; FIGS. 3C-3D show levels of inflammatory factor IL-1β in brain and peripheral tissues of zebrafish; and FIGS. 3E-3F show levels of inflammatory factor TNF-α in brain and peripheral tissues of zebrafish;

DETAILED DESCRIPTION OF EMBODIMENTS

Figure 1A:
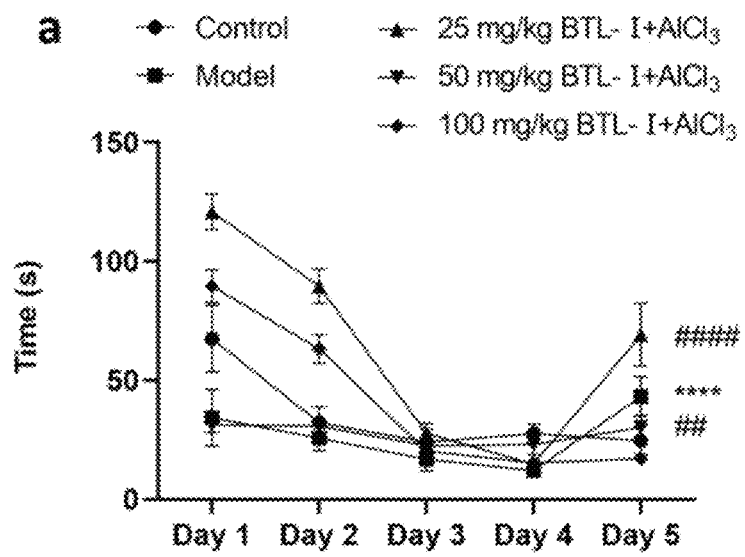
FIGS. 1A-1C are the test result of memory and cognitive disorder of zebrafish by butyrolactone-I according to the invention; in particular.

Various exemplary embodiments of the invention will now be described in detail. The detailed description should not be considered as a limitation to the invention, but should be understood as a more detailed description of certain aspects, characteristics, and embodiments of the invention.

It should be understood that the terms used in this invention are only for describing specific embodiments, and are not used to limit the invention. In addition, for the numerical range in the invention, it should be understood that each intermediate value between the upper limit and the lower limit of the range is also specifically disclosed. Any stated value or intermediate value within the stated range and any other stated value or every smaller range between intermediate values within the stated range are also included in the invention. The upper and lower limits of these smaller ranges can be independently included or excluded from the range.

Unless otherwise specified, all technical and scientific terms used herein have the same meaning as commonly understood by the ordinary technicians in the field of this invention. Although the invention only describes the preferred methods and materials, any methods and materials similar or equivalent to those described herein can also be used in the implementation or testing of the invention. All documents mentioned in this specification are incorporated by reference to disclose and describe the methods and/or materials related to the documents. In case of conflict with any incorporated documents, the contents of this specification shall prevail.

Without departing from the scope or spirit of the invention, it is obvious to those skilled in the art that many modifications and changes can be made to the specific embodiments of the invention. Other embodiments obtained from the description of the invention will be obvious to the skilled person. The specification and embodiments of this application are exemplary only.

The words "comprising", "including", "having" and "containing" used in this paper are all open terms, which mean including but not limited to.

The butyrolactone-I described in the following embodiments is prepared by fermentation, separation and purification of the marine fungus *Aspergillus terreus* C23-3 (deposited in Guangdong Microbial Culture Collection Center, GDMCC No. 60316). For the specific method, referring to Chinese patent application "Preparation method of marine fungus *Aspergillus terreus* butyrolactone compound butyrolactone-I" with the application No. 201910931305.7 (its corresponding publication No. CN110777176A).

Embodiment 1 Determination of butyrolactone-I for improving memory and cognitive disorder in zebrafish
(1) Test Method Adult wild AB zebrafish (male: female ratio is 50%: 50%) with good growth of about 6-8 months are acclimated in a 50 L water tank for 2 weeks, the temperature is 25±2° C., the light-dark cycle is 14 hours: 10 hours, and Artemia larvae are fed at 9 am and 2 pm respectively.

75 zebrafish (3.0±0.4 cm) are randomly classified into control group, $AlCl_3$ model group and 3 experimental groups with 15 zebrafish in each group, zebrafish in the experimental group are fed with food with butyrolactone-I content of 25 mg/kg, 50 mg/kg and 100 mg/kg for 20 days, zebrafish in control group and model group are fed the same amount of normal food respectively. 20 days later, after anesthesia, zebrafish in model group and experimental group are injected with $AlCl_3$ solution (4.2 mg/mL, 5 μL, pH=5.0±0.2) intraperitoneally, while zebrafish in the control group are injected with the same amount of normal saline. Memory test is performed in T maze 24 hours after injection.

Figure 1B:
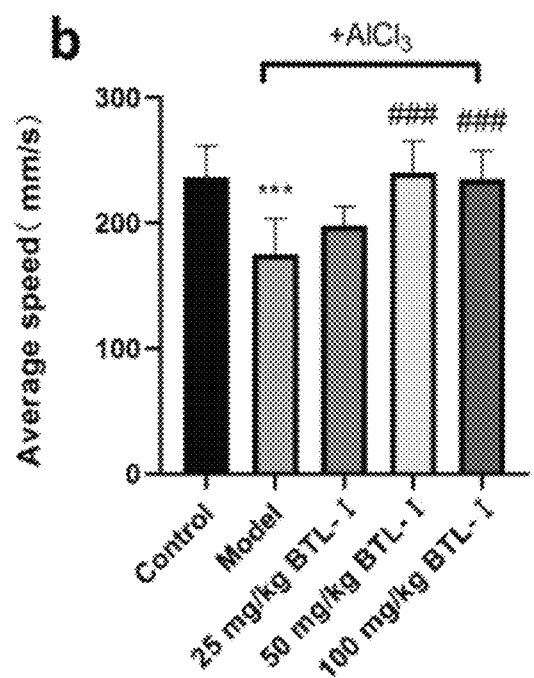
Figure 1C:
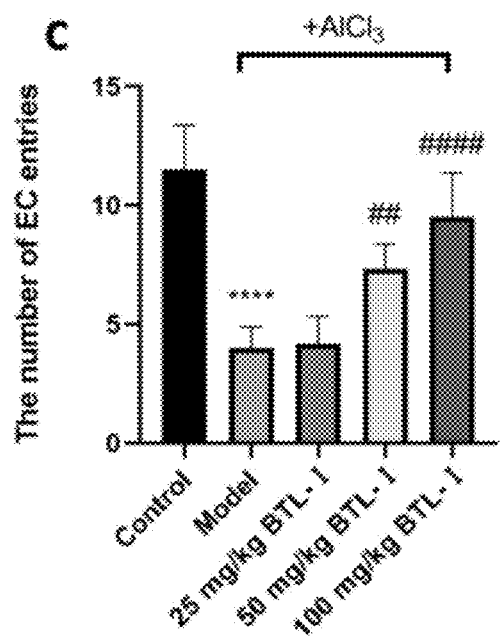
Figure 2A:
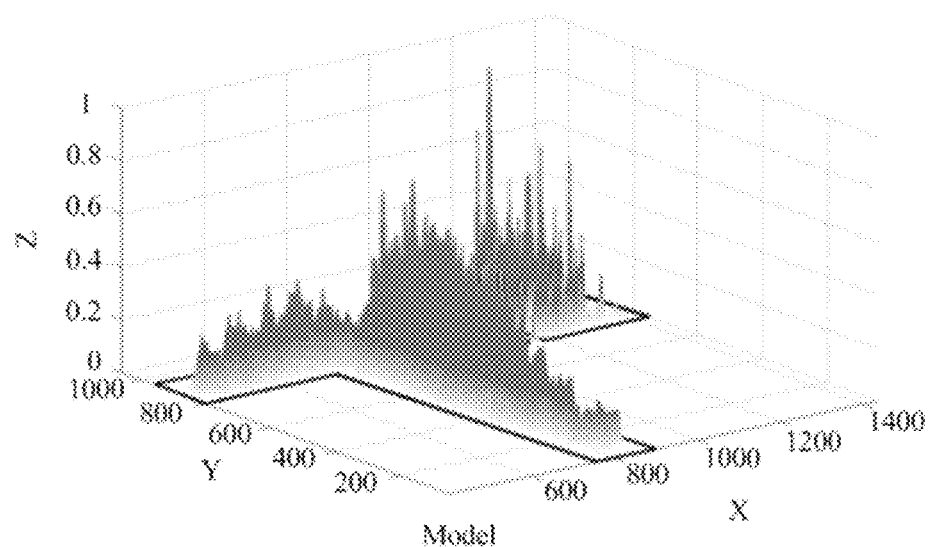
FIGS. 2A-2E are three-dimensional thermograms of butyrolactone-I reversing the behavior of zebrafish's preference for T-enriched region.
Figure 2B:
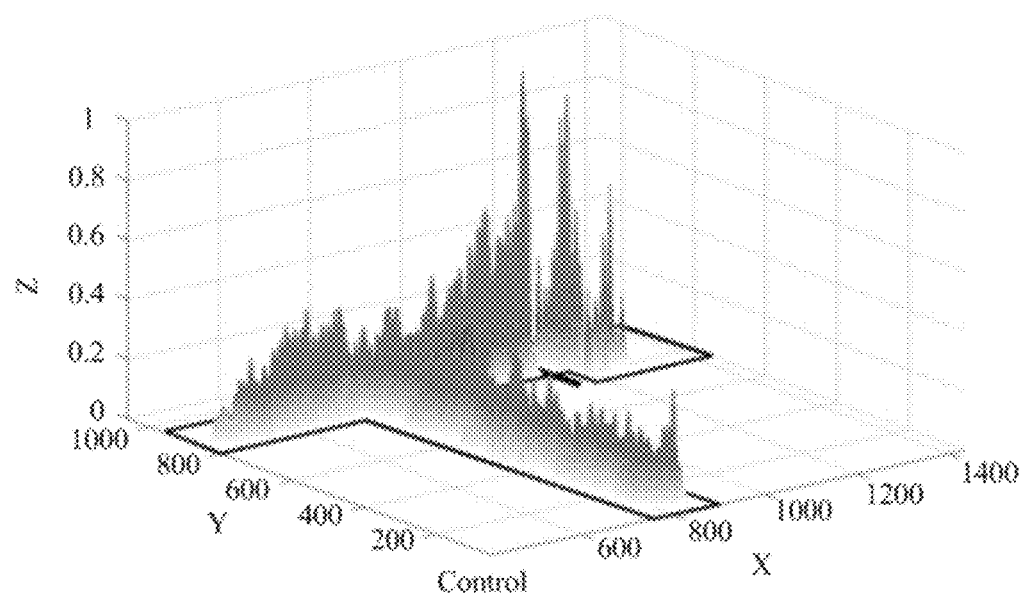
Figure 2C:
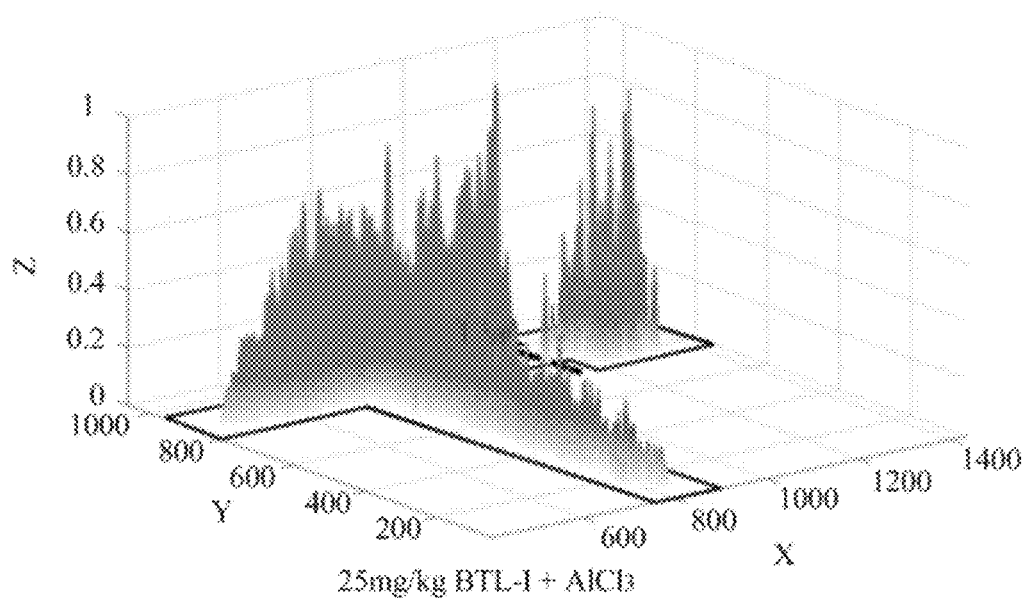
Figure 2D:
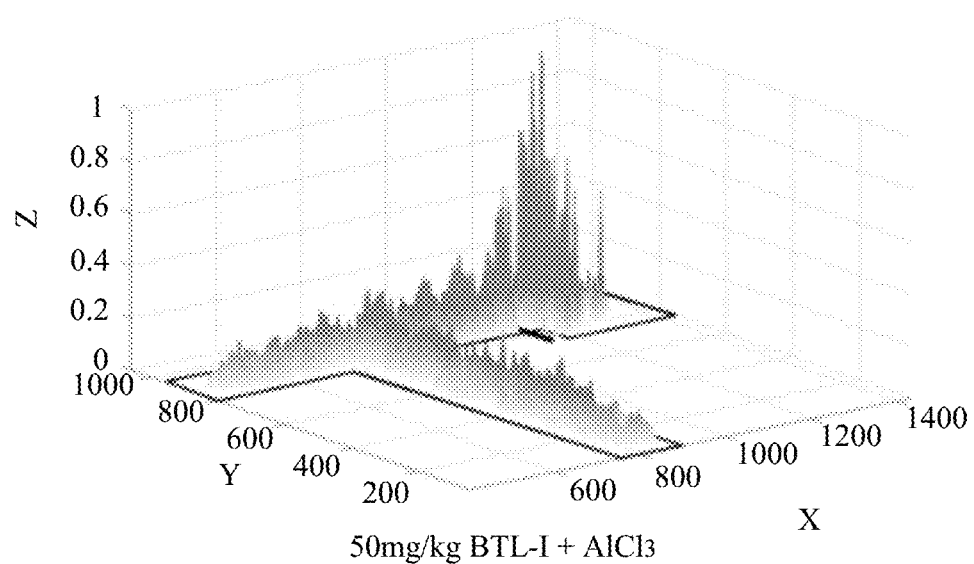
Figure 2E:
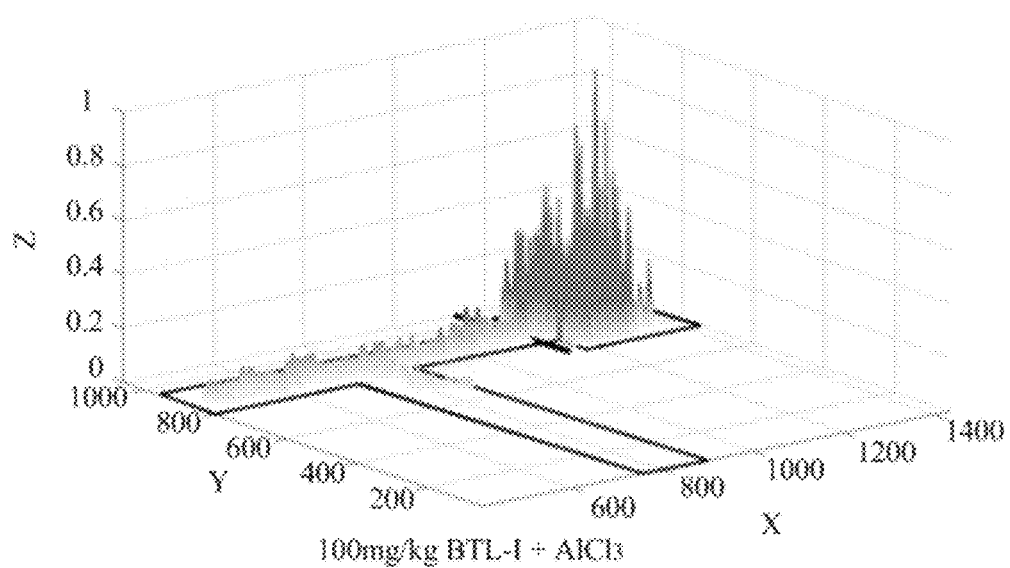

4 days before intraperitoneal injection, 6 fish are randomly selected from each group, and each day, they are trained separately in T maze for 5 minutes to find the eutrophic EC area. If one fish does not enter the eutrophic EC zone within 5 minutes, it will be led into the EC zone and stay for 30 seconds. After 4 days of training, on the 5th day (24 hours after intraperitoneal injection), the behavior of the trained fish is tested in T maze. If the fish enters EC area and stays for more than 30 s, a valid incubation period is recorded. If the fish does not enter the EC zone within 5 minutes, the incubation period is recorded as 300 s. The behavioral test is conducted between 10 am and 1 pm. The Microsoft LifeCam Studio 1080p HD camera and powersoft software (Powersoft Co., Ltd., Hong Kong, China) are used to record videos. Supersys software is used to analyze the latent time (s), average swimming speed (cm/s) and the times of entering the EC zone for the first time.
(2) Results As shown in FIGS. 1A-1C, butyrolactone-I may shorten the latent time for zebrafish to find the EC zone (FIG. 1A), increase the average swimming speed of zebrafish (FIG. 1B) and add the number of times that zebrafish enter the eutrophic EC zone (FIG. 1C) in the fifth day of T maze behavioral test. As shown in FIGS. 2A-2E, butyrolactone-I may prolong the lingering time of zebrafish in EC area.

The results show that butyrolactone-I may obviously improve the memory and cognitive disorder of zebrafish caused by aluminum trichloride, which indicates that butyrolactone-I has a potential preventive and therapeutic effect on memory disorder.

Embodiment 2 Determination method of antioxidant and anti-inflammatory biochemical indexes of butyrolactone-I
(1) Test Method 24 hours after the behavior test, the fish are euthanized, and every five fish in each group is a sample. The brain, surrounding tissues and intestines are collected and stored in a refrigerator at −80° C. All samples (except intestinal tract) are homogenized in phosphate buffer solution for further analysis. Centrifuging is conducted at 4° C. for 15 min at 1500 r/min, and the supernatant is collected. The changes of GSH level and AChE activity of tissue biomarkers are detected by using brain supernatant of zebrafish. In addition, brain samples and supernatant of peripheral tissues of zebrafish are used to determine the levels of IL-1β and TNF-α. The results are expressed by the activity of AChE per gram of protein and the amount of glutathione per gram of protein. According to OD value, the regression equation of IL-1β and TNF-α standard curves is calculated, and the logistic curve (4 parameters each) is used as a fitting model.

Graphpad Prism 8.0 is used for mapping, and One-way ANOVA and Dunnett's post hoc test are used to evaluate the differences between model group and control group, experimental group and model group.

(2) Results

Figure 3A:
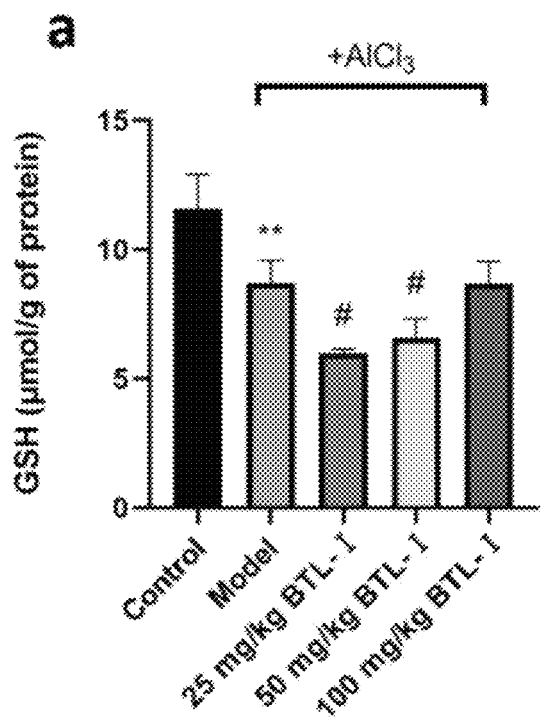
FIGS. 3A-3F are the measurement results of the antioxidant and anti-inflammatory biochemical indexes of butyrolactone-I according to the invention; in particular.
Figure 3B:
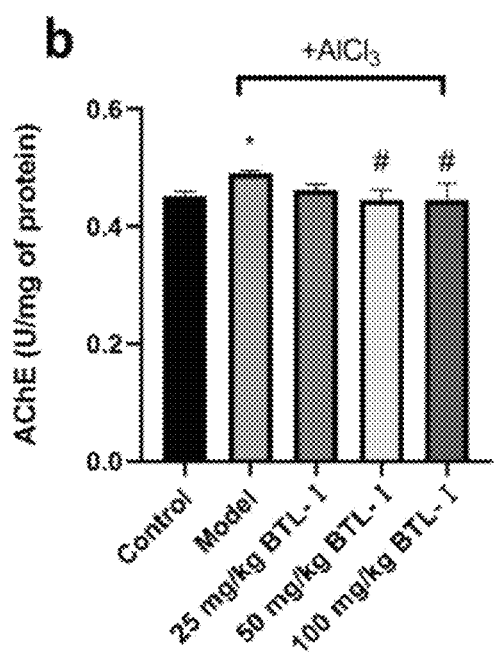
Figure 3C:
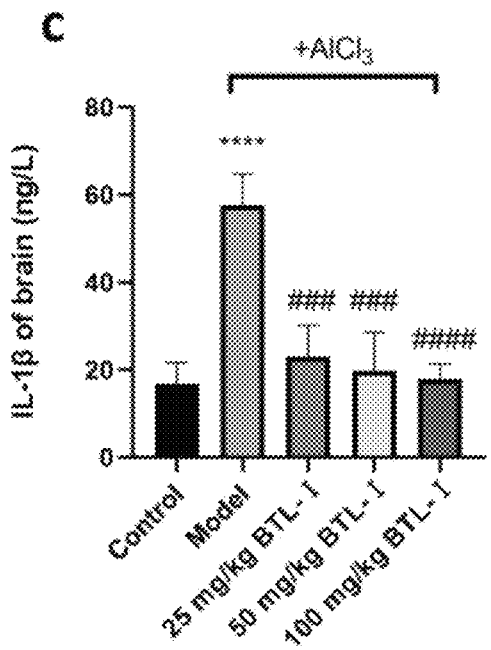
Figure 3D:
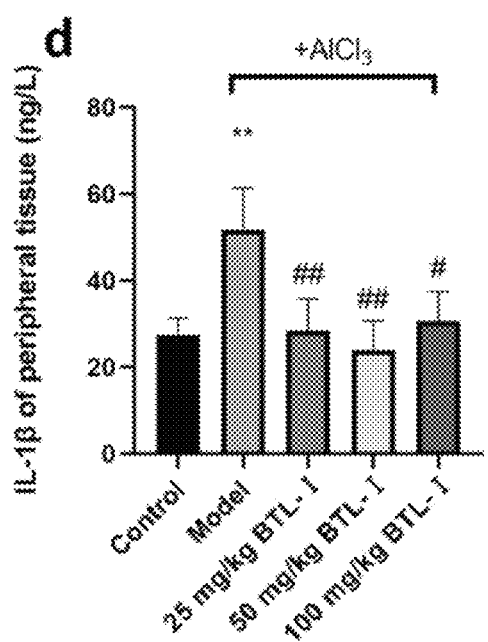
Figure 3E:
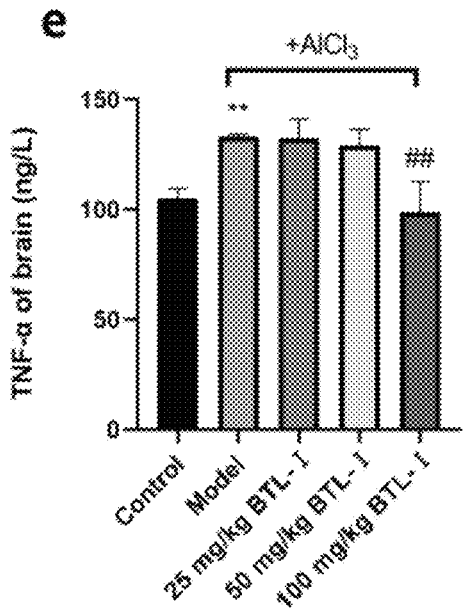
Figure 3F:
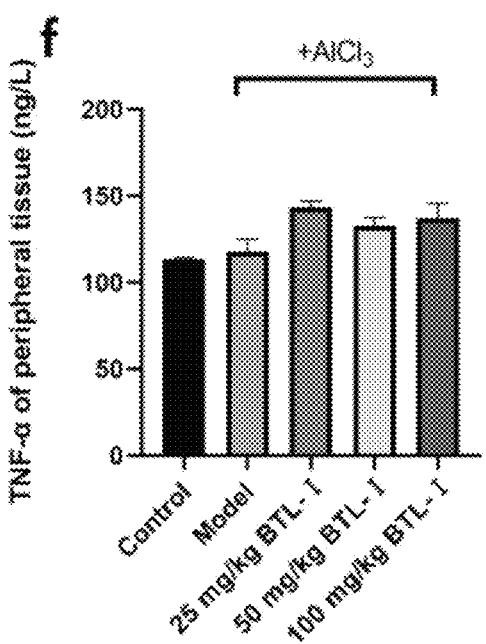

As shown in FIGS. 3A-3F, butyrolactone-I may increase GSH level in brain tissue of zebrafish in a dose-dependent manner (FIG. 3A) and inhibit AChE activity in brain tissue of zebrafish (FIG. 3B); reduce the level of inflammatory factor IL-1β in the brain and peripheral tissues of zebrafish (FIGS. 3C-3D) and inflammatory factor TNF-α in brain tissues of zebrafish (FIGS. 3E-3F).

The results show that butyrolactone-I may obviously improve the nerve inflammation of zebrafish caused by aluminum trichloride, which indicates that butyrolactone-I has potential effects of inhibiting acetylcholinesterase, resisting oxidation and resisting inflammation of brain and peripheral nerves.

Embodiment 3 Determination method of butyrolactone-I improving intestinal flora disturbance of zebrafish (1) Test Method Genomic DNA is extracted from 15 intestinal samples by proteinase K cleavage method, and sent to TinyGene Bio-Tech (ShangHai) Co., Ltd. for sequencing. The selected target gene is 16S V3-V4. According to the requirements of illumina high-throughput sequencing, two-way sequencing is carried out, and the target region and the fusion primer with "5' linker-barcode-sequencing primer-specific primer-3'" are designed. The fusion primer comprises the following primers:

The specific primer sequences are:

357F 5'-actcctacgg raggcagcag (as shown in SEQ ID NO:1)-3', where r represents a or g;

806R 5'-ggactachvg ggtwtctaat (as shown in SEQ ID NO:2)-3', where h represent a, t or c; v represents g, a or c; and w represents a or t;

F inner primer: 5'-ttccctacac gacgctcttc cgatct (as shown in SEQ ID NO:3)-actcctacgg raggcagcag (as shown in SEQ ID NO:1)-3';

F outer primer: 5'-aatgatacgg cgaccaccga gatctacac (as shown in SEQ ID NO:4)-tcttcctaca cgacgctc (as shown in SEQ ID NO:5)-3';

R inner primer: 5'-gagttccttg gcacccgaga attcca (as shown in SEQ ID NO:6)-actcctacgg raggcagcag (as shown in SEQ ID NO:1)-3';

R outer primer: 5'-caagcagaag acggcatacg agat (as shown in SEQ ID NO:7)-gtgactggag ttccttggca cccgaga (as shown in SEQ ID NO:8)-3'.

The library is constructed by a two-step PCR amplification method. First, specific primers (hereinafter described as inner primers) are used to amplify the target fragments, and then gel recovery is carried out on the target fragments. Then, the recovered products are used as templates for secondary PCR amplification (hereinafter described as outer primers for amplification). The purpose of amplification is to add the linker, sequencing primer and barcode needed by illumina platform sequencing to both ends of the target fragment.

The specific operation is as follows:

The primary PCR amplification system is shown in Table 1:

TABLE 1

| Reagents | Dosage |
| --- | --- |
| 5× Buffer | 10 μL |
| dNTP (10 mM) | 1 μL |
| Phusion ultra-fidelity DNA polymerase | 1 U |

TABLE 1-continued

| Reagents | Dosage |
| --- | --- |
| F/R inner primer (10 uM) | 1 μL each |
| Template | 5 ng-50 ng |
| ddH$_2$O | Make up to 50 μL |

The primary PCR amplification procedure is shown in Table 2:

TABLE 2

| Amplification procedure | | |
| --- | --- | --- |
| 30 cycles | 94° C. | 2 min |
| | 94° C. | 30 s |
| | 56° C. | 30 s |
| | 72° C. | 30 s |
| | 72° C. | 5 min |
| | 10° C. | Keep warm |

The secondary PCR amplification system is shown in Table 3:

TABLE 3

| Reagents | Dosage |
| --- | --- |
| 5× Buffer | 8 μL |
| dNTP (10 mM) | 1 μL |
| Phusion ultra-fidelity DNA polymerase | 0.8 U |
| F/R outer primer (10 uM) | 1 μL each |
| Template | 5 uL |
| ddH$_2$O | Make up to 40 μL |

The secondary PCR amplification procedure is shown in Table 4:

TABLE 4

| Amplification procedure | | |
| --- | --- | --- |
| 8 cycles | 94° C. | 2 min |
| | 94° C. | 30 s |
| | 56° C. | 30 s |
| | 72° C. | 30 s |
| | 72° C. | 5 min |
| | 10° C. | Keep warm |

AxyPrepDNA gel recovery kit is used for recovery, FTC-3000™ real-time PCR is used for real-time fluorescence quantification, and then Illumina high-throughput sequencing and bioinformatics analysis are performed. The length of the sequence is 450 bp, and the sequencing result is the original data, and quality of the sequence is evaluated and optimized. Trimmomatic is used for sequence filtering and FLASH for jointing. Then ambiguity, homology and some chimeras generated in PCR are screened by motherur V. 1.39.5, and the optimized sequence for subsequent clustering OTU (operational taxonomic unit) and species information analysis is obtained. Using the software USEARCH, the jointed sequences are clustered into OTU (at 97% similarity level) for later analysis.

VENN diagram may be used to count the number of common and unique OTU in multiple samples, and may intuitively show the similarity and overlap of OTU numbers of environmental samples. Usually the OTU sample table with a similar level of 97% is selected for analysis.

Alpha diversity analysis reflects the richness and diversity of communities in the sample, using Mothur (mothur.org) to calculate shannon, simpson, chao and ace indices, and using R (3.4.1) language tool to make charts.

Beta diversity analysis is used to compare the differences in species diversity between a pair of samples. The content of each group in the samples is analyzed, and then the Beta diversity value among different samples is calculated.

Analysis of community significance difference between Matastats groups, according to the obtained OTU or community abundance data, detecting the classification showing abundance difference in two groups of microbial communities, and evaluating the significance of observed differences.

Figure 4A:
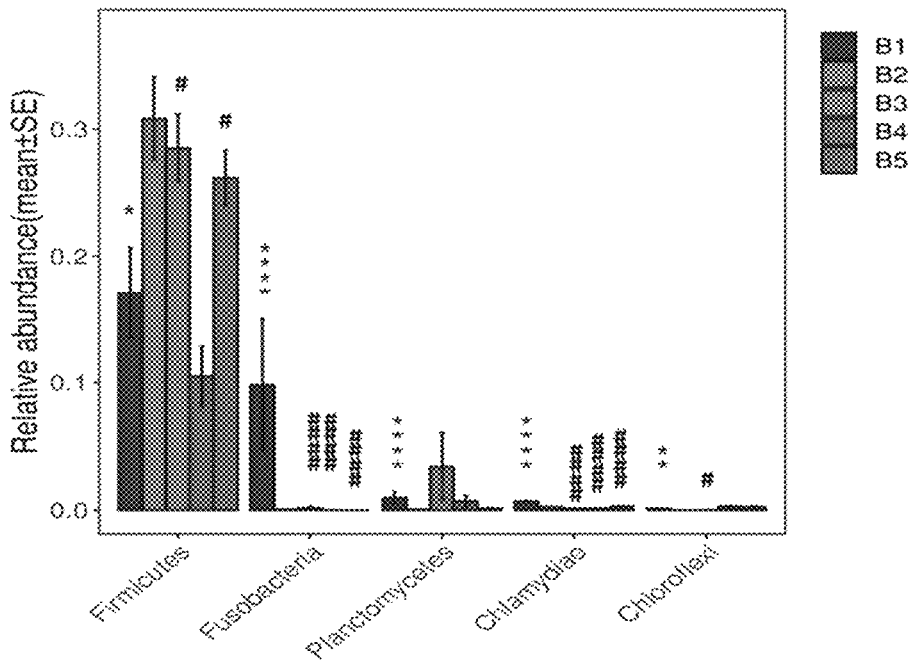
FIGS. 4A-4B are the measurement results of butyrolactone-I in improving intestinal flora disorder of zebrafish; regulating the intestinal flora disorder of zebrafish at the levels of phylum (a) and genus (b).
Figure 4B:
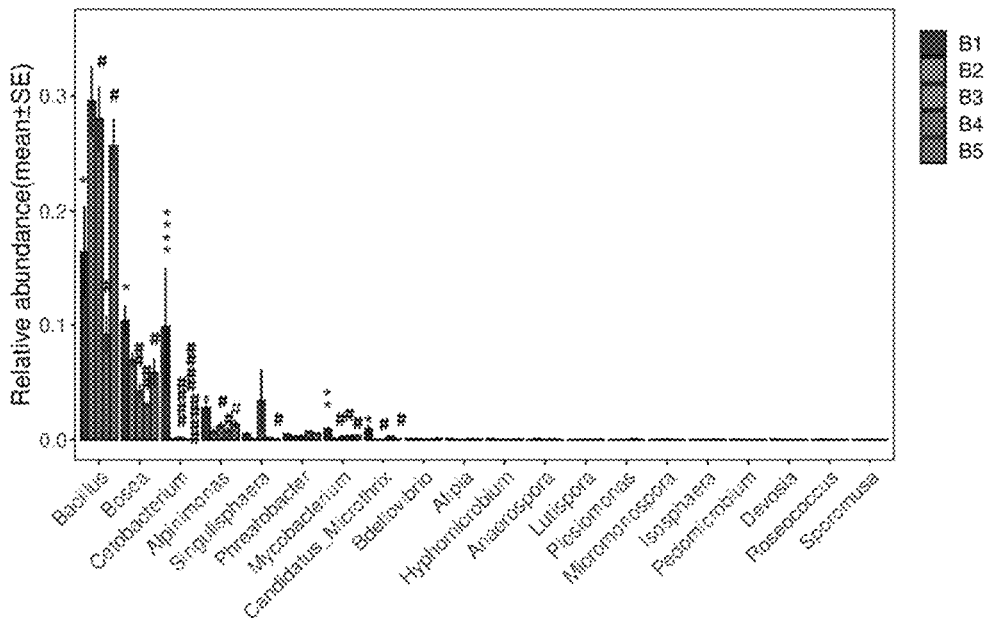

Among them, in the result charts of FIGS. 4A-4B, B1 represents aluminum trichloride model group, B2 represents normal saline control group, B3 represents oral butyrolactone-I 25 mg/kg treatment group, B4 represents oral butyrolactone-I 50 mg/kg treatment group and B5 represents oral butyrolactone-I 100 mg/kg treatment group.

(2) Results

As shown in FIGS. 4A-4B, at the phylum level, intraperitoneal injection of aluminum trichloride will reduce the abundance of Phylum Firmicutes in zebrafish intestinal microbes, and the abundance of Fusobacteria, Planctomycetes, Chlamydiae and Chloroflexi increase. Oral butyrolactone-I may up-regulate the abundance of Phylum Firmicutes and down-regulate the abundance of Fusobacterium, Planctomycetes, Chlamydiae and Chloroflexi.

At the genus level, intraperitoneal injection of aluminum trichloride will lead to the decrease of *Bacillus* abundance in intestinal microbes of zebrafish, and the abundance of *Bosea, Cetobacterium, Alpinimonas, Singulisphaera, Phreatobacter* and *Mycobacterium* increased. Oral administration of butyrolactone-I may up-regulate the abundance of *Bacillus* and down-regulate the abundance of *Bosea, Cetobacterium, Alpinimonas, Singulisphaera, Phreatobacter* and *Mycobacterium*.

The results show that butyrolactone-I may regulate the disturbance of zebrafish intestinal flora caused by aluminum trichloride, which indicates that butyrolactone-I might improve neuroinflammation and memory and cognitive disorder by regulating the disturbance of zebrafish intestinal flora.

To sum up, according to the invention, butyrolactone-I may obviously improve the memory and cognitive disorder of zebrafish caused by aluminum trichloride at the behavioral level; butyrolactone-I may significantly relieve the nerve inflammation of zebrafish caused by aluminum trichloride and inhibit the activity of acetylcholinesterase in brain at the biochemical level; and butyrolactone-I may regulate the intestinal flora disorder of zebrafish caused by aluminum trichloride at the molecular level. It is proved that butyrolactone-I may prevent aluminum-induced neuroinflammation and improve memory and cognitive disorder through the targets of antioxidation-inhibition of acetylcholinesterase activity-antiinflammation-regulation of intestinal flora disorder.

The above-mentioned embodiments only describe preferred methods of the invention, and do not limit the scope of the invention. Without departing from the design spirit of the invention, all kinds of modifications and improvements made by ordinary technicians in the field to the technical scheme of the invention should fall within the protection scope determined by the claims of the invention.

What is claimed is:

1. A method for preventing and treating aluminum-induced neuroinflammation, and/or memory and cognitive disorders in an adult zebrafish, by administering orally a pharmaceutically effective amount of a compound of butyrolactone-I.

2. The method according to claim 1, wherein the butyrolactone-I is administered to prevent and treat the aluminum-induced neuroinflammation, memory and cognitive disorders in the adult zebrafish by inhibiting acetylcholinesterase (AChE) activity.

3. The method according to claim 1, wherein the butyrolactone-I is administered to prevent and treat the aluminum-induced neuroinflammation, and/or memory and cognitive disorders in the adult zebrafish by increasing a production of glutathione (GSH) in brain.

4. The method according to claim 1, wherein the butyrolactone-I is administered to prevent and treat the aluminum-induced neuroinflammation, memory and cognitive disorders in the adult zebrafish by reducing levels of interleukin-1 beta (IL-1β) in brain and peripheral tissues and tumor necrosis factor-alpha (TNF-α) in the brain tissues of the adult zebrafish.

5. The method according to claim 1, wherein the butyrolactone-I is administered to prevent and treat the aluminum-induced neuroinflammation, memory and cognitive disorders in the adult zebrafish by improving intestinal flora disturbance of the adult zebrafish.

* * * * *

UNITED STATES PATENT AND TRADEMARK OFFICE
CERTIFICATE OF CORRECTION

| | | |
|---|---|---|
| PATENT NO. | : 12,390,443 B2 | Page 1 of 1 |
| APPLICATION NO. | : 17/675405 | |
| DATED | : August 19, 2025 | |
| INVENTOR(S) | : Zhang et al. | |

It is certified that error appears in the above-identified patent and that said Letters Patent is hereby corrected as shown below:

On the Title Page

Item (72), Lines 7-8, replace "Yongping Zhang, Zhanjiang (CN)" with "Yongping Zhang, Shenzhen (CN)".

Item (73), Lines 1-2, assignee's name from "GUANDONG OCEAN UNIVERSITY" to "GUANGDONG OCEAN UNIVERSITY".

Signed and Sealed this
Eleventh Day of November, 2025

John A. Squires
*Director of the United States Patent and Trademark Office*